United States Patent [19]

Nedelec et al.

[11] 4,009,273
[45] Feb. 22, 1977

[54] SUBSTITUTED 10,11-DIHYDRO-5,10-IMINO-[5H] DIBENZO (a,d)-CYCLOHEPTENE

[75] Inventors: Lucien Nedelec, Le Raincy; Daniel Frechet, Paris, both of France

[73] Assignee: Roussel-UCLAF, Paris, France

[22] Filed: Apr. 14, 1975

[21] Appl. No.: 568,148

Related U.S. Application Data

[62] Division of Ser. No. 328,006, Jan. 30, 1976, Pat. No. 3,892,756.

[30] Foreign Application Priority Data

Feb. 4, 1972 France .................. 72.03778

[52] U.S. Cl. .................. 424/258; 260/283 P; 260/283 R; 260/286 Q; 260/287 B; 260/288 CF; 260/289 C
[51] Int. Cl.² .................. C07D 471/08
[58] Field of Search ......... 424/258; 260/287 B, 260/289 C, 288 CF, 283 P, 283 CF, 286 Q

[56] References Cited

UNITED STATES PATENTS

| | | | |
|---|---|---|---|
| 3,597,433 | 8/1971 | Dobson | 260/287 B |
| 3,717,641 | 2/1973 | Kocsis | 260/287 B |
| 3,892,756 | 7/1975 | Nedelec et al. | 260/287 B |

Primary Examiner—Donald G. Daus
Assistant Examiner—David E. Wheeler
Attorney, Agent, or Firm—Hammond & Littell

[57] ABSTRACT

Racemates and optically active isomers of a compound selected from the group consisting of a compound of the formula

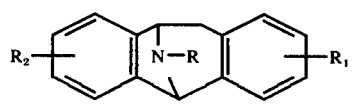

wherein R is selected from the group consisting of hydrogen, lower alkyl optionally substituted with a member of the group consisting of hydroxy and halogen, lower alkenyl, lower alkynyl, —(CH₂)ₙ— COCH₃ where n is 0 or 1,

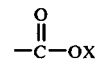

wherein X is selected from the group consisting of lower alkyl and optionally substituted phenyl, aralkyl or 7 to 8 carbon atoms, acyl of an organic carboxylic acid of 1 to 6 carbon atoms optionally substituted with

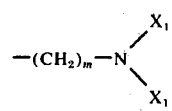

where m is an integer from 0 to 6 and X₁ is selected from the group consisting of hydrogen and lower alkyl,

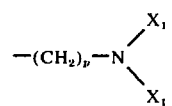

where p is an integer from 1 to 6 and X₁ is as before and

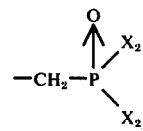

wherein X₂ is lower alkyl and R₁ and R₂ are individually selected from the group consisting of hydrogen, halogen, lower alkyl, lower alkoxy, trifluoromethyl and dilower alkylamino and the non-toxic, pharmaceutically acceptable acid addition and quaternary ammonium salts thereof which have a stimulating effect on the central nervous system while possessing at the same time anticonvulsant activity and their preparation.

12 Claims, No Drawings

SUBSTITUTED 10,11-DIHYDRO-5,10-IMINO-[5H] DIBENZO (a,d)-CYCLOHEPTENE

PRIOR APPLICATION

This application is a division of our copending, commonly assigned application Ser. No. 328,006 filed Jan. 30, 1976, now U.S. Pat. No. 3,892,756.

OBJECTS OF THE INVENTION

It is an object of the invention to provide the novel 5,10-imino-dibenzo-cycloheptenes of formula I and its acid addition salts and quaternary ammonium salts thereof.

It is another object of the invention to provide a novel process for the preparation of the dibenzocycloheptenes of formula I.

It is a further object of the invention to provide novel compositions for stimulating the central nervous system.

It is an additional object of the invention to provide a novel method of stimulating the central nervous system of warm-blooded animals.

These and other objects and advantages of the invention will become obvious from the following detailed description.

THE INVENTION

The novel products of the invention are selected from the group consisting of racemates and optically active isomers of a compound selected from the group consisting of a compound of the formula

wherein R is selected from the group consisting of hydrogen, lower alkyl optionally substituted with a member of the group consisting of hydroxy and halogen, lower alkenyl, lower alkynyl, $-(CH_2)_n-COCH_3$ where n is 0 or 1,

wherein X is selected from the group consisting of lower alkyl and optionally substituted phenyl, aralkyl of 7 to 8 carbon atoms, acyl of an organic carboxylic acid of 1 to 6 carbon atoms optionally substituted with

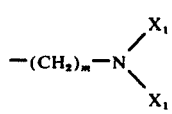

where m is an integer from 0 to 6 and $X_1$ is selected from the group consisting of hydrogen and lower alkyl,

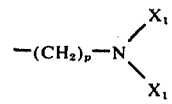

where p is an integer from 1 to 6 and $X_1$ is as before and

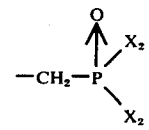

wherein $X_2$ is lower alkyl and $R_1$ and $R_2$ are individually selected from the group consisting of hydrogen, halogen, lower alkyl, lower alkoxy, trifluoromethyl and dilower alkylamino and the non-toxic, pharmaceutically acceptable acid addition and quaternary ammonium salts thereof.

The term lower alkyl is meant alkyl of 1 to 6 carbon atoms and lower alkenyl and lower alkynyl are those containing 2 to 6 carbon atoms and may be optionally substituted with halogen.

Examples of suitable acids for the non-toxic, pharmaceutically acceptable acid addition salts are mineral acids such as hydrochloric acid, sulfuric acid and organic acids, preferably of low molecular weight, such as acetic acid, propionic acid, fumaric acid, tartaric acid and benzilic acid. The quaternary ammonium salts are obtained by alkylation with a lower alkyl ester or a lower alkyl halide.

Among the preferred compounds of the invention are those where R is hydrogen, methyl, ethyl, n-propyl or hydroxyethyl and especially 10,11-dihydro-5,10-imino-[5H]-dibenzo (a,d) cycloheptene, 12-methyl-10,11-dihydro-5,10-imino-[5H]-dibenzo (a,d) cycloheptene and 12-n-propyl-10,11-dihydro-5,10-imino-[5H]-dibenzo (a,d) cycloheptene and their acid addition salts.

The process of the invention for the preparation of a dibenzocycloheptene of the formula

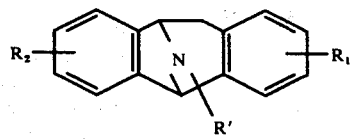

wherein $R_1$ and $R_2$ have the above definition and R' is selected from the group consisting of hydrogen, lower alkyl optionally substituted with hydroxy, lower alkenyl, lower alkynyl, $-(CH_2)_n -COCH_3$ where n is 0 or 1,

where X is lower alkyl or optionally substituted phenyl, aralkyl of 7 to 8 carbon atoms, acyl of an organic carboxylic acid of 1 to 6 carbon atoms,

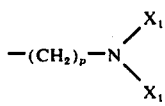

where p is 1 to 6 and $X_1$ is selected from the group consisting of hydrogen and lower alkyl and

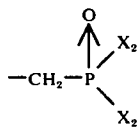

where $X_2$ is lower alkyl comprises reacting with a reducing agent a compound of the formula

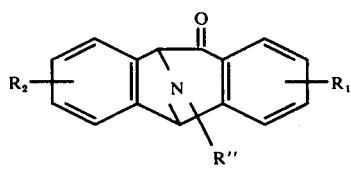

II wherein $R_1$ and $R_2$ have the above definition and R'' is selected from the group consisting of hydrogen, lower alkyl optionally substituted with hydroxy, aralkyl of 7 to 8 carbon atoms and

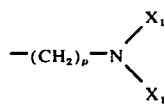

where $X_1$ and p have the above definitions to form a compound of formula Ia where R' is other than hydrogen which can be salified with a mineral or organic acid or resolved with a resolution agent or where R'' is other than hydrogen, reacted with a lower alkyl ester or a lower alkyl halide to form a quaternary ammonium salt or when R'' is hydrogen, reacted with an organic acid anhydride or a compound of the formula R'-Hal where R' is other than hydrogen and Hal is a halogen to obtain a compound of formula Ia where R' is other than hydrogen, which can be salified, resolved or transformed into a quaternary ammonium salt as before.

In a preferred mode of the invention, the reducing agent is hydrazine hydrate in the presence of an alkali metal hydroxide in the Wolff-Kishner method; but an alkali metal mixed hydride in the presence of aluminum chloride may also be used or the starting ketone may be changed to the ethylene thioketal and reduced with hydrogen in the presence of Raney nickel.

In a variation of the process of the invention, a compound of the formula

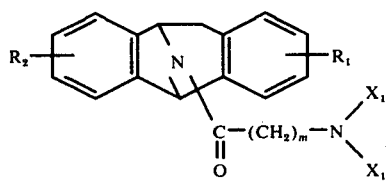

Ib wherein $R_1$, $R_2$, m and $X_1$ have the above definition is formed by reacting a compound of the formula

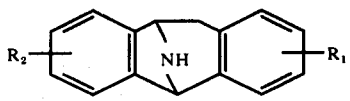

III with a halide of the formula

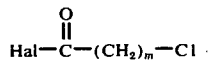

wherein Hal is bromine or chlorine to form a compound of the formula

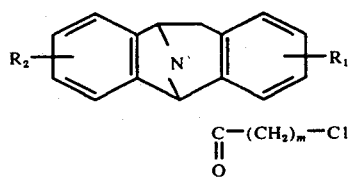

IV and reacting the latter with ammonia or a primary or secondary amine of the formula

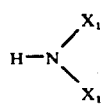

to form the compound of formula Ib which may be resolved on salified by addition of an acid. Preferably, Hal is chlorine and the amine is dimethylamine, dipropylamine or diisopropylamine.

To transform a compound of formula Ia wherein R' is methyl into the corresponding compound of formula Ia wherein R' is hydrogen, the 12-methyl derivative is reacted with an alkyl chloroformate, a cyanogen halide or ethyl azodicarboxylate to form the corresponding compound of the formula

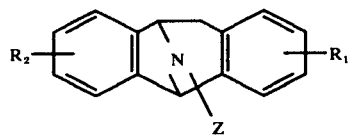

V wherein $R_1$ and $R_2$ have the above definition and Z is selected from the group consisting of

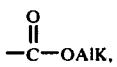

—CN and

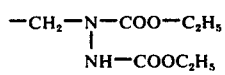

wherein Alk is lower alkyl which is hydrolyzed in acid or alkaline media to the compound of formula Ia in which R' is hydrogen. Preferably, the alkyl chloroformate is ethyl chloroformate and the hydrolysis of Z is effected in a basic media such as in the presence of an alkali metal hydroxide.

Another mode of the process of the invention for the preparation of a compound of the formula

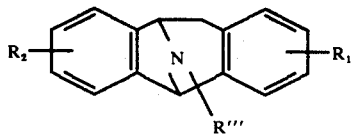 Ic wherein $R_1$ and $R_2$ have the above definition and R''' is selected from the group consisting of halo lower alkyl or

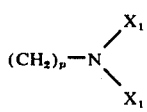

wherein $X_1$ and p have the foregoing definition comprises reacting a compound of the formula

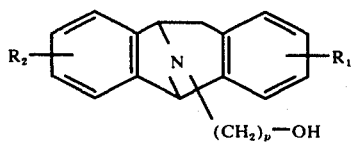 VI with a halogenating agent to form a compound of the formula

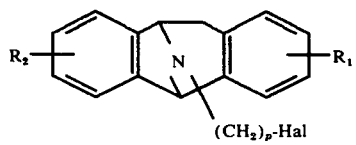 VII wherein Hal is a halogen and either reacting the latter with an acid to form the acid addition salt thereof, resolving the latter with a resolution agent or transforming the latter into a quaternary ammonium salt with a lower alkyl ester or a lower alkyl halide or reacting the compound of formula VII with an amine of the formula

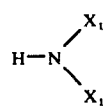

to obtain a compound the formula

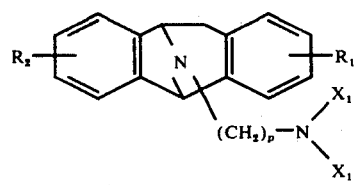 VIII which as before may be converted into the acid addition salt or quaternary ammonium salt or resolved. Preferably, the halogenation agent is thionyl chloride, sulfuryl chloride, oxalyl chloride, phosphorus pentachloride, phosphorus trichloride, phosphorus oxychloride and methane sulfonyl chloride.

In a variant of the process of the invention for producing a compound of formula Ic wherein R''' is

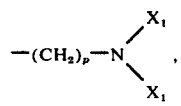

and $X_1$'s are hydrogen, the compound of formula VII is reacted with potassium phthalimide to form a compound of the formula

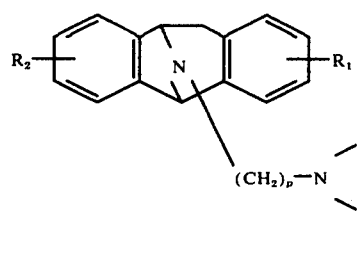 IX which is then reacted with hydrazine to obtain the desired product.

The starting materials of formula II wherein R'' is hydrogen can be obtained by the following process of reacting a dione of the formula

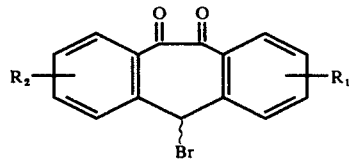 X with ammonia to obtain a compound of the formula

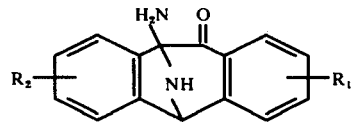 XI reacting the latter with a strong acid in aqueous media and then ammonium hydroxide to obtain a compound of the formula

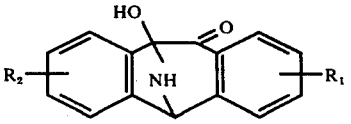 XII reacting the latter with a mixed alkali metal hydride to form a compound of the formula

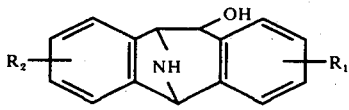

and oxidizing the latter with an oxidation agent to form the desired compound. The compound of formula XII can also be formed directly from the compound of formula X by reaction with ammonia at low temperatures.

The process of the invention for the preparation of a compound of formula II wherein R'' is other than hydrogen comprises reacting a compound of the formula

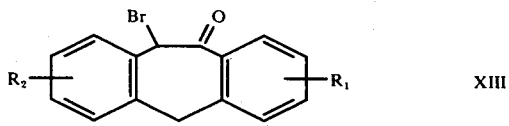   XIII with bromine to form the corresponding 5,10-dibromo compound which may then be reacted with an amine of the formula $H_2N-R''$ to form the desired compound.

The novel compositions for the stimulation of the central nervous system are comprised of an effective amount of at least one compound of formula I and their non-toxic, pharmaceutically acceptable acid addition and quaternary ammonium salts and a pharmaceutical carrier. The compositions may be in the form of injectable solutions or suspensions in the form of ampoules or multiple dose flacons or in the form of tablets, coated tablets, gelules, syrups, emulsions or suppositoires prepared in the usual manner.

The compositions are useful due their psychotonic effects for the treatment of depressive states, anxiety and emotional psychosis and for the treatment of symptoms of Parkinson disease.

The method of the invention for the stimulation of central nervous system of warm-blooded animals comprising administering to warm-blooded animals a central nervous system stimulating amount of at least one compound of formula I and their non-toxic, pharmaceutically acceptable acid addition and quaternary ammonium salts. The compounds may be administered orally, rectally or parenterally. The usual useful daily dose is 0.07 to 1.5 mg/kg depending upon the specific compound and method of administration.

In the following examples there are described several preferred embodiments to illustrate the invention. However, it is to be understood that the invention is not intended to be limited to the specific embodiments.

EXAMPLE 1

10,11-dihydro-5,10-imino-[5H]-dibenzo (a,d) cycloheptene dl

STEP A: 10-hydroxy-10,11-dihydro-5,10-imino-[5H]-dibenzo (a,d) cycloheptene-11-one dl and 10-amino-10,11-dihydro-5,10-imino[5H]dibenzo (a,d) cycloheptene-11-one dl 8 g of 5-bromo-10,11-dihydro-[5H]-dibenzo (a,d) cycloheptene-10,11-dione [prepared by process of Rigaudy et al, C. R. Acad. Sci., Vol. 246 (1958), p. 619] were added to 200 ml of ammonia at −40° C and the mixture was stirred at −40° C for 1 hour. The ammonia was distilled and the residue was taken up in 150 ml of methylene chloride. The solution was filtered and the filtrate was evaporated to dryness under reduced pressure. The oily residue was chromatographed over silica and was eluted with a 9-1 ethyl acetate-methanol mixture to obtain the 10-hydroxy derivative with a yield of 60% and the 10-amino derivative with a yield of 40%. Crystallization of the 10-hydroxy derivative from ethyl acetate gave pure 10-hydroxy-10,11-dihydro-5,10-imino-[5H]-dibenzo (a,d) cycloheptene-11-one dl melting at 214° C.

Analysis: $C_{15}H_{11}NO$; molecular weight = 237.25 Calculated: %C 75.93 %H 4.67 %N 5.90 Found; 75.6 4.6 6.2

Crystallization of the 10-amino derivative from ether gave the pure 10-amino-10,11-dihydro-5,10-imino-[5H]-dibenzo (a,d) cycloheptene-11-one dl melting at 171° C.

Analysis: $C_{15}H_{12}N_2O$; molecular weight = 236.26 Calculated: %C 76.25 %H 5.12 %N 11.86 Found: 76.3 4.9 11.7

STEP B: 11-hydroxy-10,11-dihydro-5,10-imino-[5H]-dibenzo (a,d) cycloheptene dl cis 8 g of 10-hydroxy-10,11-dihydro-5,10-imino-[5H]-dibenzo (a,d) cycloheptene-11-one dl were added at 10° C to 400 ml of dioxane containing 16 g of lithium aluminum hydride and the mixture was refluxed for 3 days. 8 g of lithium aluminum hydride were added thereto and the mixture was refluxed for another 48 hours and after cooling, 700 ml of tetrahydrofuran, 150 ml of isopropanol, 50 ml of water and then 250 ml of concentrated hydrochloric acid were added thereto. The tetrahydrofuran and the dioxane were distilled off and 1000 ml of methylene chloride containing 20% methanol were added thereto. The mixture was made alkaline with sodium hydroxide addition and was extracted with methylene chloride containing 20% methanol. The extracts were washed with water, dried over magnesium sulfate and concentrated to dryness. The oil residue was dissolved in methylene chloride and the solution was washed with 2N hydrochloric acid. The combined acid wash waters were made alkaline with sodium hydroxide and extracted twice with ether. The ether solution was washed with water, dried over magnesium sulfate and concentrated to dryness under reduced pressure. The residue was chromatographed over silica gel and was eluted with a 92.5–7.5 chloroform-methanol mixture. Crystallization from methylene chloride gave 11-hydroxy-10,11-dihydro-5,10-imino-[5H]-dibenzo (a,d) cycloheptene dl cis melting at 200° and then 210° C.

Analysis: $C_{15}H_{13}NO$; molecular weight=223.26 Calculated: %C 80.69 %H 5.87 %N 6.27 Found: 80.3 5.7 6.6

STEP C: 10,11-dihydro-5,10-imino-[5H]-dibenzo(a,d)cycloheptene-11-one dl 2.7 g of active manganese dioxide were added to a suspension of 5.4 g of the product of Step B in 80 ml of chloroform and the mixture was stirred at room temperature. After 7 hours and after 15 hours of contact, each time 2.7 g of manganese dioxide were added thereto. The mixture was stirred for 96 hours and the precipitate formed was recovered by filtration, was washed three times with 2N hydrochloric acid and then water. The acid aqueous phase was made alkaline with sodium hydroxide and was then extracted with ether. The ether phase was washed with water, then dried and evaporated to dryness. The residue was chromatographed over silica gel and eluted with a 9-1 chloroform-methanol mixture. The product was crystallized from ether to obtain 10,11-dihydro-5,10-imino-[5H]-dibenzo (a,d) cycloheptene-11-one dl.

STEP D: 10,11-dihydro-5,10-imino-[5H]-dibenzo (a,d) cycloheptene dl

A mixture of 1.55 g of the product of Step C, 15 ml of ethylene glycol and 0.7 ml of hydrazine hydrate was heated at 100° C for 1 hour and after adding 1.25 g of potassium hydroxide pellets thereto, the mixture was heated at 160°–165° C for 2½ hours and then cooled. Water was added thereto and the mixture was extracted with ether. The ether phase was washed with water, dried over magnesium sulfate and distilled to dryness under reduced pressure. The residue was added to 5 ml of ether and the mixture was vacuum filtered. The precipitate was washed with isopropyl ether and 4 g of the product were dissolved in 120 ml of hot ether. The mixture was filtered and the filtrate was concentrated to 20 ml. Crystallization was effected overnight at room temperature and the precipitate was recovered by vacuum filtration, was washed with ether and dried to obtain 3 g of 10,11-dihydro-5,10-imino-[5H]-dibenzo (a,d) cycloheptene dl melting at 120° C.

Analysis: $C_{15}H_{13}N$ = 207.26 Calculated: %C 86.92 %H 6.32 %N 6.76 Found: 87.1 6.3 6.9

EXAMPLE 2

10-hydroxy-10,11-dihydro-5,10-imino-[5H]-dibenzo (a,d) cycloheptene-11-one dl

A current of ammonia was bubbled through a solution of 100 mg of 5-bromo-10,11-dihydro-[5H]-dibenzo (a,d) cycloheptene-10,11-dione in 60 ml of tetrahydrofuran for 7 hours at room temperature and then the mixture was distilled to dryness under reduced pressure. The residue was taken up in 5 ml of methylene chloride and the mixture was filtered. The filtrate was evaporated to dryness under reduced pressure and the residue was empasted with ether, vacuum filtered and dried to obtain 78 mg of 10-amino-10,11-dihydro-5,10-imino-[5H]-dibenzo (a,d) cycloheptene-11-one dl.

A solution of 100 mg of the said product in 1.5 ml of N hydrochloric acid was stirred for 30 minutes at room temperature and was made alkaline by ammonium hydroxide addition. The mixture was extracted with methylene chloride and the organic phase was washed with water, dried over magnesium sulfate and distilled to dryness under reduced pressure. The residue was empasted with ether, vacuum filtered and dried to obtain 90 mg of 10-hydroxy-10,11-dihydro-5,10-imino-[5H]-dibenzo (a,d) cycloheptene-11one dl melting at 212° C.

EXAMPLE 3

10 g of 5-bromo-10,11-dihydro-[5H]-dibenzo (a,d) cycloheptene-10,11-dione was added to 250 ml of ammonia cooled to −40° C and then stirred for 1 hour at −40° C. The ammonia was distilled off and after adding 100 ml of 5 N hydrochloric acid thereto, the mixture was heated at 60°–65° C for 30 minutes. The mixture was cooled, made alkaline with addition of 110 ml of ammonium hydroxide and extracted with methylene chloride. The organic phase was washed with water, dried over magnesium sulfate and distilled to dryness under reduced pressure. The residue was crystallized from ether, vacuum filtered and dried to obtain 7.4 g of 10-hydroxy-10,11-dihydro-5,10-imino-[5H]dibenzo (a,d) cycloheptene-11-one dl melting at 214° C.

EXAMPLE 4

A mixture of 1.5 g of 11-hydroxy-10,11-dihydro-5,10-imino-[5H]-dibenzo (a,d) cycloheptene dl cis, 60 ml of benzene and 3 g of silver silicate was refluxed with stirring for 45 minutes and then 1.5 g of silver silicate were added and reflux was continued for another hour. The mixture was filtered hot and the filter was washed with methylene chloride. The combined filtrates were washed with 2N hydrochloric acid and the acid phase was made alkaline with sodium hydroxide. The mixture was extracted with methylene chloride and the organic phase was dried over magnesium sulfate and distilled to dryness under reduced pressure. The residue was chromatographed over silica gel and eluted with a 95-5 mixture of chloroform-methanol to obtain 780 mg of 10,11-dihydro-5,10-imino-[5H]-dibenzo (a,d) cycloheptene-11-one dl melting at 100° C identical to that of Example 1.

EXAMPLE 5

The process of Step B of Example 1 was repeated but instead of chromatography of the final product, the product was crystallized from ether to obtain 1.2 g of raw product consisting of 10,11-dihydro-5,10-imino-[5H]-dibenzo (a,d) cycloheptene dl and its 11-hydroxylated derivative melting at 155° C and 180° C. The mixture was chromatographed over silica gel and was eluted with 92.5 – 7.5 chloroform-methanol mixture. The residue was crystallized from ether to obtain 10,11-dihydro-5,10-imino-[5H]-dibenzo (a,d) cycloheptene dl melting at 120° C and identical to the product of Step D in Example 1.

EXAMPLE 6

12-(2′-hydroxyethyl)-10,11-dihydro-5,10-imino-[5H]-dibenzo (a,d) cycloheptene dl A mixture of 2.5 g of 10,11-dihydro-5,10-imino-[5H]-dibenzo (a,d) cycloheptene dl, 25 ml of ethanol, 2.5 g of potassium carbonate and 2 ml of monochlorohydrin of glycol was refluxed for 1 hour under a nitrogen atmosphere and 0.5 ml of monochlorohydrin of glycol were added thereto. After 2 hours of reflux, another 0.5 ml of monochlorohydrin of glycol was added and the mixture was refluxed for another hour for a total of 4 hours. After cooling, the reaction mixture was added to water and extracted with methylene chloride. The organic phase was washed with 2N hydrochloric acid and the acid phase was made alkaline by addition of sodium hydroxide. The mixture was extracted with ether and the ether phase was washed with water, dried over magnesium sulfate and distilled to dryness. The residue was washed with ether and dried to obtain 2 g of 12-(2′-hydroxyethyl)-10,11-dihydro-5,10-imino-[5H]-dibenzo (a,d) cycloheptene dl which after crystallization from isopropylether occurred as a colorless solid melting at 105° C and then 116° C.

Analysis: $C_{17}H_{17}NO$; molecular weight = 251.31 Calculated: %C 81.24 %H 6.82 %N 5.57 Found: 81.3 6.9 5.4

EXAMPLE 7

12-acetonyl-10,11-dihydro-5,10-imino-[5H]-dibenzo (a,d) cycloheptene dl

A mixture of 2 g of 10,11-dihydro-5,10-imino-[5H]-dibenzo (a,d) cycloheptene dl, ml of of ethanol, 2.5 g of potassium carbonate and 1.5 ml of chloroacetone was refluxed under a nitrogen atmosphere and after 2 hours of reflux, 0.5 ml of chloroacetone were added and again after another 2 hours of reflux, 0.5 ml of chloroacetone was added. The mixture was refluxed for 2 more hours (total of 6 hours) and after cooling, water was added to the reaction mixture. The mixture was extracted with ether and the ether phase was washed with 2N hydrochloric acid. The acid phase was made alkaline by addition of sodium hydroxide and was extracted with ether. The ether phase was washed with water, was treated with activated carbon, was filtered, dried over magnesium sulfate and distilled to dryness. The residue was chromatographed over silica gel and was eluted with a 9-1 chloroform-methanol mixture. The product was crystallized from isopropyl ether and then ether to obtain 1.52 g of 12-acetonyl-10,11-dihydro-5,10-imino-[5H]-dibenzo (a,d) cycloheptene dl melting at 128°-130° C.

Analysis: $C_{18}H_{17}NO$; molecular weight = 263.32 Calculated: %C 82.10 %H 6.51 %N 5.32 Found: 81.7 6.5 5.2

EXAMPLE 8

12-(o-nitrophenoxycarbonyl)-10,11-dihydro-5,10-imino-[5H]-dibenzo (a,d) cycloheptene dl A mixture of 2.25 g of 10,11-dihydro-5,10-imino-[5H]-dibenzo (a,d) cycloheptene dl, 5 ml of hexamethylphosphotriamide and 5 ml of benzene was formed under a nitrogen atmosphere and a solution of 2.46 g of o-nitrophenyl chloroformate in 5 ml of benzene was added thereto at room temperature. The mixture was refluxed for 2 hours and then distilled to dryness under reduced pressure. The residue was added to 25 ml of water and the mixture was extracted with methylane chloride. The organic phase was washed with 2N hydrochloric acid, with water, with an aqueous 10% sodium carbonate solution and finally with water, dried over magnesium sulfate and distilled to dryness. The residue was crystallized from ether to obtain 3.2 g of 12-(o-nitrophenoxycarbonyl)-10,11-dihydro-5,10-imino-[5H]-dibenzo (a,d) cycloheptene dl melting at 140° C.

Analysis: $C_{22}H_{16}N_2O_4$; molecular weight = 372.37
Calculated: %C 70.95 %H 4.33 %N 7.52
Found: 71.1 4.5 7.2

EXAMPLE 9

12-dimethylphosphorosomethyl-10.11-dihydro-5,10-imino-[5H]-dibenzo (a,d) cycloheptene dl A mixture of 2.25 g of 10,11-dihydro-5,10-imino-[5H]dibenzo (a,d) cycloheptene dl, 30 ml of toluene and 5.4 g of dimethylchloromethylphosphinoxide [prepared by process of King et al, Inorg. Chem., Vol. 4 (1965), p. 198] was refluxed under a nitrogen atmosphere and 15 ml of toluene were distilled off and maintaining reflux for 4 hours. The toluene was evaporated under reduced pressure and 50 ml of water and a few drops of sodium hydroxide were added thereto. The mixture was extracted with methylene chloride and the organic phase was washed with water, dried over magnesium sulfate and distilled to dryness. The residue was chromatrographed over silica gel and eluted with a 9-1 chloroform-methanol mixture to obtain 2.2 g of 12-dimethylphosphorosomethyl-10,11-dihydro-5,10-imino-[5H]-dibenzo (a,d) cycloheptene dl melting at 150° C.

Analysis: $C_{18}H_{20}NOP$; molecular weight = 297.37
Calculated: %C 72.69 %H 6.78 %N 4.71
Found: 72.4 6.9 5.1

EXAMPLE 10

12-acetyl-10,11-dihydro-5,10-imino-5H]-dibenzo (a,d) cycloheptene dl 4 ml of acetic acid anhydride were added under a nitrogen atmosphere to a mixture of 2 g of 10,11-dihydro-5,10-imino-[5H]-dibenzo (a,d) cycloheptene dl and 6 ml of pyridine cooled to 0° C and the mixture was stirred for 1 hour at room temperature. 20 ml of water were added thereto and the mixture was stirred for 30 minutes. The mixture was extracted with methylene chloride and the organic phase was washed with 2N hydrochloric acid, then with water, dried over magnesium sulfate and distilled to dryness. The residue was dissolved in a refluxing mixture of 40ml of ether and 20 ml of methylene chloride and the mixture was concentrated to the beginning of crystallization. The mixture stood overnight and was vacuum filtered. The precipitate was washed with ether and dried under reduced pressure to obtain 1.8 g of 12-acetyl-10,11-dihydro-5,10-imino-[5H]-dibenzo (a,d) cycloheptene dl melting at 188° C.

Analysis: $C_{17}N_{15}NO$; molecular weight = 249.30
Calculated: %C 81.90 %H 6.06 %N 5.62
Found: 81.7 6.4 5.3

EXAMPLE 11

12-(2'-dimethylaminoethyl)-10.11-dihydro-5,10-imino-[5H]-dibenzo (a,d) cycloheptene dl A mixture of 500 mg of 10,11-dihydro-5,10-imino-[5H]-dibenzo (a,d) cycloheptene dl, 1 of hexamethylphosphotriamide and 0.35 ml of 2-dimethylaminoethyl chloride was heated at 120° C with stirring for 4 hours and after cooling the mixture, 30 ml of methylene chloride were added thereto. The mixture was extracted with N hydrochloric acid and the acid phase was made alkaline with sodium hyroxide and extracted with ether. The ether phase was washed with water, dried over magnesium sulfate and distilled to dryness under reduced pressure. The residue was chromatographed over silica gel and eluted with a 1-1 chloroform-methanol mixture to obtain 270 mg of 12(2'-dimethylaminoethyl)-10,11-dihydro-5,10-imino-[5H]-dibenzo (a,d) cycloheptene dl in the form of an amorphous product.

Analysis: $C_{19}H_{22}N_2$; molecular weight > 278.39
Calculated: %C 81.97 %H 7.97 %N 10.06
Found: 82.0 8.2 9.9

| U. V. Spectrum (ethanol): | | |
|---|---|---|
| Inflex. towards 227 nm | $E^{1\%}_{1cm} = 320$ | |
| Inflex. towards 257 nm | $E^{1\%}_{1cm} = 27$ | |
| Inflex. towards 262 nm | $E^{1\%}_{1cm} = 37$ | |
| Max. at 269 nm | $E^{1\%}_{1cm} = 51$ | $\epsilon = 1420$ |
| Max. at 276 nm | $E^{1\%}_{1cm} = 59$ | $\epsilon = 1640$ |

I. R. Spectrum (chloroform):

EXAMPLE 12

12-(3'-dimethylaminopropyl)-10,11-dihydro-5,10-imino-[5H]-dibenzo (a,d) cycloheptene dl A mixture of 500 mg of 10,11-dihydro-5.10-imino-[5H]-dibenzo (a,d) cycloheptene dl, 5 ml of hexamethylphosphotriamide, 500 mg of potassium carbonate and 2 ml of 3-dimethylaminopropyl chloride was heated at 105° C for 1 hour and then 0.5 ml of 3-dimethylaminopropyl chloride was added and heating was continued for 30 minutes. After cooling, the mixture was poured into water and was extracted with methylene chloride. The organic phase was washed with 2N hydrochloric acid, then with water, and the acid phase was made alkaline with sodium hydroxide and extracted with ether. The ether phase was washed with water, dried over magnesium sulfate and evaporated to dryness to obtain 440 mg of 12-(3'-dimethylaminopropyl)-10,11-dihydro-5,10-imino-[5H]-dibenzo (a,d) cycloheptene dl which when crystallized from pentane melted at 74° C.

Analysis: $C_{20}H_{24}N_2$; molecular weight = 292.41
Calculatedl: %C 82.14 %H 8.27 %N 9.58
Found: 8.19 8.1 9.3

EXAMPLE 13

12-carbamoyl-10,11-dihydro-5,10-imino-[5H]-dibenzo (a,d) cycloheptene dl 19 ml of toluene containing 20% phosgene were added to a mixture of 1.8 g of 10,11-dihydro-5,10-imino-[5H]-dibenzo (a,d) cycloheptene dl, 20 ml of toluene and 0.7 ml of triethylamine cooled to 0° C and the mixture was stirred for 15 minutes at room temperature and filtered. The filter was washed with toluene and the filtrate was evaporated to dryness under reduced pressure. The residue was taken up in 20 ml of benzene and the solution was evaporated to dryness to obtain 2.3 g of 12-chlorocarbonyl-10,11-dihydro-5,10-imino-[5H]-dibenzo (a,d) cycloheptene dl melting at 139-140° C (calculated %Cl 13.14 — Found 12.9).

The 2.3 g of product were dissolved in 30 ml of tetrahydrofuran and a current of ammonia was bubbled therethrough for 8 hours at room temperature while adding a few ml of tetrahydrofuran to maintain a constant volume of 30 ml. After purging with nitrogen, the mixture was extracted with methylene chloride and the organic phase was washed with water, dried over magnesium sulfate and distilled to dryness under reduced pressure. The residue was washed with ether and dried to obtain 1.52 g of 12-carbamoyl-10,11-dihydro-5,10-imino-[5H]-dibenzo (a,d) cycloheptene dl melting at 193° C.

Analysis: $C_{16}H_{14}N_2O$; moleculre weight = 250.29
Calculated: %C 76.77 %H 5.64 %N 11.19
Found: 76.6 5.7 11.3

EXAMPLE 14

12-dimethylaminoacetyl-10,11-dihydro-5,10-imino-[5H]-dibenzo (a,d) cycloheptene dl STEP A: 12-chloroacetyl-10,11-dihydro-5,10-imino-[5H]-dibenzo (a,d) cycloheptene dl 1 ml of monochloroacetyl chloride was added to a solution of 500 mg of 10,11-dihydro-5,10-imino-[5H]-dibenzo (a,d) cycloheptene dl in 5 ml of methylene chloride and after stirring for 18 hours at room temperature, the mixture was poured into water and was extracted with methylene chloride. The organic phase was washed with N sodium hydroxide, dried over magnesium sulfate and distilled to dryness under reduced pressure. The residue was crystallized from ether to obtain 550 mg of 12-chloroacetyl-10,11-dihydro-5,10-imino-[5H]-dibenzo (a,d) cycloheptene dl melting at 146° C.

Analysis: $C_{17}H_{14}ClNO$; molecular weight = 283.75
Calculated: %C 71.95 %H 4.97 %Cl 12.50 %N 4.93
Found: 71.9 4.8 12.4 5.0

STEP B: 12-dimethylaminoacetyl-10,11-dihydro-5,10-imino-[5H]-dibenzo (a,d) cycloheptene dl A solution of 2.3 g of 12-chloroacetyl-10,11-dihydro-5,10-imino-[5H]-dibenzo (a,d) cycloheptene dl in 100 ml of dimethylamine was stirred for 2 hours and excess dimethylamine was distilled off. The residue was added to 100 ml of water and the mixture was extracted with methylene chloride. The organic phase was washed with water, dried over magnesium sulfate and distilled to dryness under reduced pressure to obtain 2.2 g of 12-dimethylaminoacetyl-10,11-dihydro-5,10-imino-[5H]-dibenzo (a,d) cycloheptene dl melting at 132° C.

Analysis: $C_{19}H_{20}N_2O$; molecular weight = 297.37
Calculated: %C 78.05 %H 6.90 %N 9.57
Found: 77.9 6.7 9.7

EXAMPLE 15

12-methyl-10,11-dihydro-5,10-imino-[5H]-dibenzo (a,d) cycloheptene dl

STEP A: 10-Bromo-10,11-dihydro-[5H]-dibenzo (a,d) cycloheptene-11-one

A solution of 1.34 ml of bromine in 10 ml of carbon tetrachloride was added to a solution of 5 g of 10,11-dihydro-[5H]-dibenzo (a,d) cycloheptene-11-one in 60 ml of carbon tetrachloride cooled to 0° C and after stirring for 30 minutes at room temperature, the insolubles were filtered off. The filtrate was distilled to dryness under reduced pressure to obtain 6.6 g of raw product which was crystallized from methanol to obtain 10-bromo-10,11-dihydro-[5H]-dibenzo (a,d) cycloheptene-11-one melting at 82°–84° C. The product was identical to that described by Rigaudy et al [Bull. Soc. Chim., 1959, p. 638].

STEP B: 5,10-dibromo-10,11-dihydro-[5H]-dibenzo (a,d) cycloheptene-11-one

A solution of 900 mg of the product of Step A in 9 ml of carbon tetrachloride was cooled to 5° C and with irradiation (h') 0.22 ml of bromine dissolved in 4 ml of carbon tetrachloride was added thereto. The mixture was stirred for 7 hours while permitting the interior temperature to rise to 50° C and excess reactant was removed with a current of nitrogen to obtain a solution of 5,10-dibromo-10,11-dihydro-[5H]-dibenzo (a,d) cycloheptene-11-one which was used as is for the next step.

STEP C: 12-methyl-10,11-dihydro-5,10-imino-[5H]-dibenzo (a,d) cycloheptene-11-one dl A ml of a solution of methylamine in methylene chloride (titrating: 31 g/liter) was added to the solution of Step B and after stirring for 30 minutes, 25 ml of water were added thereto. The mixture was extracted with methylene chloride and the organic phase was washed with water, dried over magnesium sulfate and evaporated to dryness under reduced pressure. The residue was chromatographed over silica gel and eluted with a n-3 benzene-ethyl acetate mixture. The residue was empasted with isopropyl ether to obtain 220 mg of 12-methyl-10,11-dihydro-5,10-imino-[5H]-dibenzo (a,d) cycloheptene-11-one dl melting at 90° C.

STEP D: 12-methyl-10,11-dihydro-5,10-imino-[5H]-dibenzo (a,d) cycloheptene dl

A mixture of 5 g of 12-methyl-10,11-dihydro-5,10imino-[5H]-dibenzo (a,d) cycloheptene-11-one dl, 50 ml of ethyleneglycol and 2 ml of hydrazine hydrate was heated to 100°–105° C for 1 1/2 hours and after the addition of 3.75 g of potassium hydroxide pellets, the mixture was heated for 3 hours at 165°–170° C. After cooling, 100 ml of water were added thereto and the mixture was extracted with ether. The ether phase was washed with water, dried over magnesium sulfate and distilled to dryness. The residue was chromatographed over silica gel and eluted with a 95-5 chloroform-methanol mixture. The residue was dissolved in 40 ml of hot pentane and filtered and concentrated to 10 ml. Crystallization was effected overnight at room temperature and the mixture was vacuum filtered. The crystals were washed with iced pentane and dried and crystallized from pentane to obtain 2.5 g of 12-methyl-10,11-dihydro-5,10-imino[5H]-dibenzo (a,d) cycloheptene dl melting at 78° C.

Analysis: $C_{16}H_{15}N$; molecular weight = 221.29
Calculated: %C 86.84 %H 6.83 %N 6.33
Found 87.1 6.7 6.6

EXAMPLE 16

12-methyl-10,11-dihydro-5,10-imino-[5H]-dibenzo (a,d) cycloheptene dl iodomethylate 1 ml of methyl iodide in 5 ml of ether were added under nitrogen atmosphere to a solution of 2.2 g of 12-methyl -10,11-dihydro-5,10-imino-[5H]-dibenzo (a,d) cycloheptene dl in 30 ml of ether and after stirring 2 hours at room temperature, another 0.5 ml of methyl iodide was added. The mixture was stirred overnight at room temperature and was vacuum filtered. The product recovered was washed with ether, crystallized from methanol and dried to obtain 2.05 of 12-methyl-10,11-dihydro-5,10-imino-[5H]-dibenzo (a,d) cycloheptene dl iodomethylate melting at 305°–306° C. Concentration of the mother liquor gave a second crop of 0.26 g of the product.

Analysis: $C_{17}H_{18}NI$; molecular weight = 363.23
Calculated: %C 56.21 %H 4.99 %N 3.85 %I 34.94
Found: 56.0 4.9 3.9 34.7

EXAMPLE 17

12-carbethoxy-10,11-dihydro-5,10imino-[5H]-dibenzo (a,d) cycloheptene dl

A mixture of 2 g of 12 -methyl-10,11-dihydro-5,10-imino-[5H]-dibenzo (a,d) cycloheptene dl, 40 ml of benzene and 3 ml of ethyl chloroformate was refluxed under a nitrogen atmosphere for 6 hours and then was distilled to dryness under reduced pressure. The residue was taken up in 200 ml of ether and the ether phase was washed with 2N hydrochloric acid and then water, dried over magnesium sulfate and distilled to dryness under reduced pressure. The residue was washed with ether and dried to obtain 1.9 g of 12-carbethoxy-10,11-dihydro-5,10-imino-[5H]-dibenzo (a,d) cycloheptene dl. After crystallization from ether, it melted at 113° C.

Analysis: $C_{18}H_{17}NO_2$; molecular weight = 279.32
Calculated: %C 77.39 %H 6.13 %N 5.01
Found: 77.2 6.0 5.3

EXAMPLE 18

10,11-dihydro-5,10-imino-[5H]-dibenzo (a,d) cycloheptene dl

A mixture of 12 g of 12-carbethoxy-10,11-dihydro-5,10 -imino-[5H]-dibenzo (a,d) cycloheptene dl, 240 ml of ethanol, 24 ml of water and 24 g of potassium hydroxide pellets was refluxed under nitrogen for 16 hours and the ethanol was evaporated under reduced pressure. The mixture was extracted with ether and the etheral phase was washed with water, dried over magnesium sulfate and distilled to dryness under reduced pressure. The residue was washed with ether to obtain 8.4 g of 10,11-dihydro-5,10-imino-[5H]-dibenzo (a,d) cycloheptene dl melting at 120° C, identical to the product of Example 1.

EXAMPLE 19

12-allyl-10,11-dihydro-5,10-imino-[5H]-dibenzo (a,d) cyclo-heptene dl

First 2.5 g of 10,11-dihydro-5,10-imino-[5H]-dibenzo (a,d) cycloheptene dl and then 1.25 g of silver oxide were added to 25 ml of chloroform and after cooling to 0° C, 1.5 ml of allyl bromide were added. The mixture was stirred for 2 hours at 0° C and then was filtered. The filtrate was concentrated to dryness under reduced pressure and the residue was chromatographed over silica gel and eluted with a 9-1 chloroform-methanol mixture. The product was crystallized from pentane to obtain 1.8 g of 12-allyl-10,11-dihydro-5,10-imino-[5H]-dibenzo (a,d) cycloheptene dl. Another crystallization from pentane resulted in a product melting at 110° C, then 114° C.

Analysis: $C_{18}H_{17}N$; molecular weight = 247.32
Calculated: %C 87.41 %H 6.93 %N 5.66
Found: 87.1 6.7 5.5

EXAMPLE 20

12-propargyl-10,11-dihydro-5,10-imino-[5H]-dibenzo (a,d) cycloheptene dl

A mixture of 5 g of 10,11-dihydro-5,10-imino-[5H]-dibenzo (a,d) cycloheptene dl, 50 ml of benzene, 2.5 g of sodium bicarbonate and 2.5 ml of propargyl bromide was refluxed under nitrogen for 1 ½ hours and after cooling, the mixture was filtered. The filtrate was evaporated to dryness and the residue was taken up in 200 ml of methylene chloride. The organic phase was washed with 2N hydrochloric acid and the acid solution was made alkaline with cold sodium hydroxide. The mixture was extracted with ether and the ether phase was washed with water, dried over magnesium sulfate and distilled to dryness. The residue was crystallized from isopropyl ether and dried to obtain 2.4 g of 12-propargyl-10,11 -dihydro-5,10-imino-[5H]-dibenzo (a,d) cycloheptene dl melting at 120°–121° C.

Analysis: $C_{18}H_{15}N$; molecular weight = 245.31

Calculated: %C 88.13 %H 6.16 %N 5.71
Found: 88.4 6.1 5.9

EXAMPLE 21

12-ethyl-10,11-dihydro-5,10-imino-[5H]-dibenzo (a,d) cycloheptene dl

A mixture of 4 g of 10,11-dihydro-5,10-imino-[5H]-dibenzo (a,d) cycloheptene dl, 25 ml of chloroform, 2 g of silver oxide and 1.7 ml of ethyl iodide was stirred for 3 hours at room temperature and after the addition of another 0.35 ml of ethyl iodide, the mixture was stirred for 3 hours. Another 0.35 ml of ethyl iodide and 0.5 g of silver oxide were added and the mixture was stirred overnight at room temperature. The mixture was filtered and the filtrate was concentrated to dryness. The residue was taken up in 100 ml of methylene chloride and the organic phase was washed with 2N hydrochloric acid. The acid filtrate was made alkaline with cold sodium hydroxide and was extracted with ether. The ether phase was washed with water, dried over magnesium sulfate and distilled to dryness. The residue was crystallized from pentane to obtain 2.8 g of 12-ethyl-10,11-dihydro-5,10-imino-[5H]-dibenzo (a,d) cycloheptene dl melting at about 84° C.

Analysis: $C_{17}H_{17}N$; molecular weight = 235.31
Calculated: %C 86.77 %H 7.28 %N 5.95
Found: 86.6 7.2 6.0

EXAMPLE 22

12-n-butyl-10,11-dihydro-5,10-imino-[5H]-dibenzo (a,d) cycloheptene dl and its hydrochloride A mixture of 3.5 g of 10,11-dihydro-5,10-imino-[5H]-dibenzo (a,d) cycloheptene dl, 3.5 g of potassium carbonate and 35 ml of acetone was prepared under a nitrogen atmosphere at room temperature and after the addition of 2.3 ml of n-butyl iodide, the mixture was stirred for 7 hours while adding 3 times 0.3 ml of butyl iodide. The mixture was filtered and the filtrate was evaporated to dryness under reduced pressure. The residue was extracted with N hydrochloric acid and the acid aqueous phase was washed with ether and made alkaline with sodium hydroxide. The mixture was extracted with methylene chloride and the organic phase was washed with water, dried over magnesium sulfate and distilled to dryness to obtain 3.6 g of raw product. The latter was chromatographed over silica gel to obtain 3.5 g of 12-n-butyl-10,11-dihydro-5,10-imino-[5H]-dibenzo (a,d) cycloheptene dl in the form of an oil. The oil was dissolved in 20 ml of ethyl acetate and ethyl acetate saturated with hydrochloric acid was added thereto. The precipitate crystallized from methylene chloride to obtain 2.4 g of the hydrochloride of the product melting at 260° C.

Analysis: $C_{19}H_{22}ClN$; molecular weight = 299.84
Calculated: %C 76.10 %H 7.40 %N 4.67 %Cl 11.83
Found: 76.1 7.3 4.8 12.1

EXAMPLE 23

12-benzyl-10,11-dihydro-5,10-imino-[5H]-dibenzo (a,d) cycloheptene dl

A mixture of 3 g of 10,11-dihydro-5,10-imino-[5H]-dibenzo (a,d) cycloheptene dl, 3 g of potassium carbonate, 30 ml of ethanol and 2.1 ml of benzyl bromide under nitrogen was stirred for 1 ½ hours at room temperature and then the ethanol was distilled under reduced pressure. The residue was taken up in ether and the ether phase was extracted with 2N hydrochloric acid. The acid phase was made alkaline with sodium hydroxide and was extracted with ether. The ether phase was washed with water, dried over magnesium sulfate and distilled to dryness under reduced pressure to obtain 4 g of an oil which was crystallized from pentane to obtain 3.8 g of 12-benzyl-10,11-dihydro-5,10-imino-[5H]-dibenzo (a,d) cycloheptene dl which melted at 90°–92° C after crystallization from isopropyl ether.

Analysis: $C_{22}H_{19}N$; molecular weight = 297.38
Calculated: %C 88.85 %H 6.44 %N 4.71
Found: 88.9 6.5 4.8

EXAMPLE 24

12-n-propyl-10,11-dihydro-5,10-imino[5H]-dibenzo (a,d) cycloheptene dl

A mixture of 4 g of 10,11-dihydro-5,10-imino-[5H]-dibenzo (a,d) cycloheptene dl, 40 ml of acetone, 4 g of potassium carbonate and 2 ml of n-propyl iodide under nitrogen stood for 1 hour at room temperature and then in 4 hours, 4 doses of 0.5 ml of n-propyl iodide were added thereto. The mixture was filtered and the acetone was distilled off under reduced pressure. The raw product was taken up in 200 ml of methylene chloride and the latter was extracted with 2N hydrochloric acid. The acid phase was made alkaline with sodium hydroxide and was then extracted with ether. The ether phase was washed with water, dried over magnesium sulfate and distilled to dryness to obtain 4.1 g of raw product. The latter was crystallized from pentane to obtain 3 g of 12-n-propyl-10,11-dihydro-5,10-imino-[5H]-dibenzo (a,d) cycloheptene dl melting at 80° C.

Analysis: $C_{18}H_{19}N$; molecular weight = 249.34
Calculated: %C 86.70 %H 7.68 %N 5.62
Found: 86.5 7.6 5.6

EXAMPLE 25

12-(methylaminoacetyl)-10,11-dihydro-5,10-imino-[5H]-dibenzo (a,d) cycloheptene dl 10 ml of monomethylamine in methylene chloride (titrating 167 g/liter) were added under a nitrogen atmosphere to 5 g of 12-chloroacetyl-10,11-dihydro-5,10-imino-[5H]-dibenzo (a,d) cycloheptene dl in 50 ml of methylene chloride and after stirring for 2 hours at room temperature, excess monomethylamine was distilled off under reduced pressure. The residue was taken up in methylene chloride and the solution was washed with water, dried over magnesium sulfate and distilled to dryness under reduced pressure. The recovered oil was added to 100 ml of hot ether and the solution was treated with activated carbon, filtered and distilled to dryness under reduced pressure. The residue was chromatographed over silica gel and eluted with a 55 chloroform-methanol mixture to obtain 3.35 g of 12-(methylaminoacetyl)-10,11-dihydro-5,10-imino-[5H]-dibenzo(a,d) cycloheptene dl as an amorphous solid.

Analysis: $C_{18}H_{18}N_2O$; molecular weight = 278.34
Calculated: %C 77.67 %H 6.52 %N 10.07
Found: 77.5 6.8 9.8

EXAMPLE 26

8-chloro-12-methyl-10,11-dihydro-5,10-imino-[5H]-dibenzo (a,d) cycloheptene dl and its fumarate A mixture of 3.35 g of 8-chloro-12-methyl-10,11-dihydro-5,10-imino-[5H]-dibenzo (a,d) cycloheptene-11-one dl (prepared by process of Steps A to C of Example 15 but starting from 8-chloro-10,11-dihydro-[5H]-dibenzo (a,d)cycloheptene-11-one)melting at 108° C, 35 ml of ethyleneglycol and 1.3 ml of hydrazine hydrate under a nitrogen atmosphere was heated at 115° C for 1 ¼ hours and then 2.55 g of potassium hydroxide pellets were added. The mixture was heated at 175° C for 2 hours and after cooling, 100 ml of water were added. The mixture was extracted with methylene chloride and the organic phase was washed with water, dried over magnesium sulfate and concentrated to dryness under reduced pressure to obtain 3.5 g of raw product. The latter was chromatographed over silica gel and eluted with a 9-1 chloroform-methanol mixture to obtain 2.35 g of 8-chloro-12-methyl-10,11-dihydro-5,10-imino-[5H]-dibenzo (a,d) cycloheptene dl. The product was dissolved in 20 ml of ethyl acetate, and then 1 g of fumaric acid in 20 ml of methanol was added thereto. The mixture was concentrated under a slight pressure and crystallization was effected. The mixture was vacuum filtered and the precipitate was washed with ethyl acetate and dried under reduced pressure to obtain 3.1 g of the fumarate of the said 8-chloro compound melting at 148°–150° C.

Analysis: $C_{20}H_{18}ClNO_4$; molecular weight = 371.80
Calculated: %C 64.60 %H 4.88 %N 3.77 %Cl 9.54
Found: 64.3 4.9 3.8 9.5

EXAMPLE 27

12-(2′-chloroethyl)-10,11-dihydro-5,10-imino-[5H]-dibenzo (a,d) cycloheptene dl A mixture of 4 g of 12-(2′-hydroxyethyl)-10,11-dihydro-5,10-imino-[5H]-dibenzo (a,d) cycloheptene dl and 40 ml of thionyl chloride was refluxed under a nitrogen atmosphere for 1 hour and then excess thionyl chloride was distilled off under reduced pressure. 60 ml of benzene were added and the mixture was distilled to dryness under reduced pressure. The residue was taken up in 200 ml of methylene chloride and the solution was made alkaline with 20 ml of triethylamine. The mixture was extracted with methylene chloride and the organic phase was washed with water, dried over magnesium sulfate and distilled to dryness under reduced pressure. The residue was taken up in ether, vacuum filtered and recrystallized from ether to obtain 2.7 g of 12-(2′-chloroethyl)-10,11-dihydro-5,10-imino-[5H]-dibenzo (a,d) cycloheptene dl melting at 110° C.

Analysis: $C_{17}H_{16}ClN$; molecular weight = 269.75
Calculated: %C 75.68 %H 5.98 %Cl 13.15 %N 5.19
Found: 75.7 6.1 13.4 5.5

EXAMPLE 28

12-(2′-methylaminoethyl)-10,11-dihydro-5,10-imino-[5H]-dibenzo (a,d) cycloheptene dl 100 ml of condensed monomethylamine were added to a 150 ml autoclave and 3.5 g of 12-(2′-chloroethyl)-10,11-dihydro-5,10-imino-[5H]-dibenzo (a,d) cycloheptene dl were added thereto. The mixture was heated for 24 hours at 95° C with stirring and after cooling, excess monomethylamine was distilled off. The residue was added to methylene chloride and the solution was washed with water, dried over magnesium sulfate and concentrated to dryness under reduced pressure to obtain 3.3 g of raw product. The latter was chromatographed over silica gel and eluted with a 65-30-5 chloroform-methanol-triethylamine mixture to obtain 2.8 g of product. The product was taken up in 100 ml of refluxing ether and the solution was filtered and distilled to dryness to obtain 2.4 g of 12-(2′-methylaminoethyl)-10,11-dihydro-5,10-imino-[5H]-dibenzo (a,d) cycloheptene dl melting at 48°–50° C.

Analysis: $C_{18}H_{20}N$; molecular weight = 264.36
Calculated: %C 81.78 %H 7.63 %N 10.60
Found: 81.6 7.7 10.3

EXAMPLE 29

12-(2′-dimethylaminoethyl)-10,11-dihydro-5,10-imino-[5H]-dibenzo (a,d) cycloheptene dl and its fumarate 3.9 g of 12-(2′-chloroethyl)-10,11-dihydro-5,10-imino-[5H]-dibenzo (a,d) cycloheptene dl and 100 ml of dimethylamine were added with agitation at 0° C to a 150 ml autoclave and after heating at 70° C for 15 hours, the mixture was cooled and dimethylamine was distilled at room temperature. The residue was taken up in methylene chloride and the organic solution was washed with water, dried over magnesium sulfate and distilled to dryness under reduced pressure to obtain 3.8 g of raw product. The latter was chromatographed over silica gel and eluted with a 5-5 chloroform-methanol mixture to obtain 2.8 g of 12-(2′-dimethylaminoethyl)-10,11-dihydro-5,10-imino-[5H]-dibenzo (a,d) cycloheptene dl as an oil. The oil was dissolved in 30 ml of ethyl acetate and a solution of 1.27 g of fumaric acid in 20 ml of methanol was added dropwise. Then 20 ml of ethyl acetate were added and the mixture was concentrated to 20 ml. The mixture was vacuum filtered to obtain 4 g of product which was crystallized from an ethyl acetate-methanol mixture to obtain 3.1 g of the fumarate of the dimethylaminoethyl product melting at 180° C.

Analysis: $C_{23}H_{26}N_2O_4$; molecular weight = 394.45
Calculated: %C 70.03 %H 6.64 %N 7.10
Found: 69.9 6.7 6.9

EXAMPLE 30

12-(2′-aminoethyl)-10,11-dihydro-5,10-imino-[5H]-dibenzo (a,d) cycloheptene dl STEP A: 12-(2′-phthalimidoethyl)-10,11-dihydro-5,10-imino-[5H]-dibenzo (a,d) cycloheptene dl A mixture of 4 g of 12-(2′-chloroethyl)-10,11-dihydro-5,10-imino-[5H]-dibenzo (a,d) cycloheptene dl, 20 ml of dimethylformamide and 2.9 g of potassium phthalimide was heated with stirring under a nitrogen atmosphere for 1¼ hours and after cooling the mixture, 50 ml of water were added. The precipitate formed was recovered by vacuum filteration, was washed with water and taken up in 200 ml of ether. The organic solution was washed with water, dried over magnesium sulfate and distilled to dryness under reduced pressure. The residue was taken up in ether, vacuum filtered and dried under reduced pressure to obtain 4.7 g of 12-(2′-phthalimidoethyl)-10,11-dihydro-5,10-imino-[5H]-dibenzo (a,d) cycloheptene dl melting at 150° C. The product was used as is for the next step.

STEP B: 12-(2′-aminoethyl)-10,11-dihydro-5,10-imino-[5H]-dibenzo (a,d) cycloheptene dl A mixture of 4.7 g of 12-(2'-phthalimidoethyl)-10,11-dihydro-5,10-imino-[5H]-dibenzo (a,d) cycloheptene dl, 47 ml of methanol and 1 ml of hydrazine hydrate was refluxed with stirring under a nitrogen atmosphere for 1 hour and after cooling, the precipitate formed was recovered by vacuum filtration and was washed with methanol. The filtrate was distilled to dryness under reduced pressure and the residue was taken up in methylene chloride. The solution was extracted with 2N hydrochloric acid and the acid extract was made alkaline with sodium hydroxide. The mixture was extracted with ether and the ether phase was washed with water, dried over magnesium sulfate and distilled to dryness under reduced pressure to obtain 3.1 g of raw product. The latter was dissolved in 100 ml of refluxing ether and the solution was treated with activated carbon, filtered and concentrated. THe crystals formed were recovered by vacuum filtration and were washed with ether to obtain 2.6 g of 12-(2'-aminoethyl)-10,11-dihydro-5,10-imino-[5H]-dibenzo (a,d) cycloheptene dl melting at 82°–83° C.

Analysis: $C_{17}H_{18}N_2$; molecular weight = 250.33 Calculated: %C 81.56 %H 7.25 %N 11.19 Found: 81.5 7.1 11.6

PHARMACOLOGICAL STUDY

A. Amphetamine Toxicity

The test was effected on group of 10 female mice weighing between 18 and 22 g kept at 27° C for the duration of the test. The test products were intraperitoneally administered in different doses in a volume of 0.01 ml /g of mouse. One hour later, the mice received an injection of 15 mg/kg of a solution of 1.5 mg of amphetamine per ml of physiological serum. The mortality 4 hours after the amphetamine injection was determined and the results were expressed as a ratio of number of dead animals to number of starting animals. The $DA_{50}$ dose, the dose which reduced by half the amphetamine deaths, was determined and the results are reported in Table I.

The results of Table I show that the products clearly reduced the deaths provoked by amphethamine, particularly 12-methyl-10,11-dihydro-5,10-imino-[5H]-dibenzo (a,d) cycloheptene dl which had a $DA_{50}$ of 1 mg/kg.

B. Anticonvulsant Effect

The anticonvulsant activity of the compounds was determined on groups of 10 female mice with intraperitoneal administration of the test compounds in acid solution at different doses and the control group received only the solvent. One hour after the injection, the mice were perfused with a solution of pentamethylenetetrazol in physiological serum at a concentration of 3 mg/ml. The perfusion was intraveinous at a rate of 1 ml per minute and in the course of the perfusion, the progress of introxication was characterized by the following 3 criteria:

a. Threshold of convulsant effect (myoclonia of the ears)

b. Crisis of clonic convulsions c. Tonic convulsion with apnea and generally followed by death.

The dose of pentamethylenetetrazol corresponding to these effects was noted and the results are reported in Table II.

TABLE I

| Product | Controls | 200γ/Kg | 500γ/Kg | 1 mg/Kg | 2 mg/Kg | 5 mg/Kg | 10 mg/Kg | 20 mg/Kg | mg/Kg |
|---|---|---|---|---|---|---|---|---|---|
| Example 15 | 10/10 | 10/10 | 8/10 | 6/10 | 1/10 | 0/10 | 0/10 | | |
| Examples 1 and 18 | 9/10 | 9/10 | 9/10 | 10/10 | 5/10 | | | | |
| Example 6 | 10/10 | | | | | 3/10 | 9/10 3/10 | 0/10 | |
| Example 7 | 8/10 | | | | | 2/10 | 0/10 | 0/10 | 0/10 |
| Example 21 | 10/10 | | | | | 10/10 | 6/10 | 0/10 | 0/10 |
| Example 20 | 10/10 | | | | 9/10 | 9/10 | 7/10 | 1/10 | |
| Example 24 | 6/10 | | | | | 10/10 | 9/10 | 3/10 | |
| Example 26 | 10/10 | | | | | 10/10 | 10/10 | 10/10 | 1/9 |
| Example 27 | 8/10 | | | | | 10/10 | 8/10 | 2/10 | |

TABLE II

| Group | Dose Administred | Dose of pentamethylenetetrazol in mg/Kg | | |
|---|---|---|---|---|
| | | Myoclonia | Clonic Crisis | Tonic Crisis |
| Controls | 0 | 43.3 | 48.1 | 110.1 |
| 12-propargyl-10,11-dihydro-5,10-imino-[5H]-dibenzo (a,d) cycloheptene dl | 0.5 mg/Kg | 44.2 | 49.1 | 140.7 |
| | 1 mg/Kg | 41.9 | 46.7 | 146.4 |
| | 2 mg/Kg | 41.2 | 46.2 | 168.5 |
| | 5 mg/Kg | 43.9 | 49.0 | 221.7 |
| Controls | 0 | 40.1 | 44.6 | 139.0 |
| 12-acetonyl-10,11-dihydro-5,10-imino-[5H]-dibenzo (a,d) cycloheptene dl | 0.5 mg/Kg | 48.6 | 53.3 | 119.2 |
| | 1 mg/Kg | 47.7 | 52.7 | 172.5 |
| | 2 mg/Kg | 57.7 | 62.6 | 172.5 |
| | 5 mg/Kg | 107.4 | 112.5 | 238.9 |
| Controls | 0 | 40.3 | 46.4 | 124.9 |
| 12-ethyl-10,11-dihydro-5,10-imino-[5H]-dibenzo (a,d) cycloheptene dl | 1 mg/Kg | 42.9 | 48.3 | 168.2 |
| | 2 mg/Kg | 42.3 | 47.7 | 206.2 |
| | 5 mg/Kg | 49.6 | 57.0 | 238.1 |
| Controls | 0 | 43.4 | 48.7 | 130.7 |
| 12-allyl-10,11-dihydro-5,10-imino-[5H]-dibenzo (a,d) cycloheptene dl | 2 mg/Kg | 44.8 | 50.0 | 150.8 |
| | 5 mg/Kg | 44.5 | 49.8 | 136.0 |
| | 10 mg/Kg | 47.4 | 52.4 | 241.9 |
| | 20 mg/Kg | 49.2 | 54.7 | 271.8 |
| Controls | 0 | 33.7 | 38.3 | 75.7 |
| 12-(2'-hydroxyethyl)-10,11-dihydro-5,10-imino-[5H]-dibenzo (a,d) cycloheptene dl | 0.5 mg/Kg | 38.2 | 42.9 | 129.0 |
| | 1 mg/Kg | 40.6 | 45.7 | 144.2 |
| | 2 mg/Kg | 38.6 | 43.5 | 104.3 |
| | 5 mg/Kg | 49.3 | 45.5 | 204.6 |
| Controls | 0 | 34.9 | 40.3 | 90.4 |
| 12-methyl-10,11-dihydro-5,10-imino-[5H]-dibenzo (a,d) cycloheptene | 200γ/Kg | 38.1 | 43.0 | 122.7 |
| | 500γ/Kg | 41.1 | 45.9 | 134.9 |
| | 1 mg/Kg | 38.1 | 44.0 | 182.7 |
| | 2 mg/Kg | 46.7 | 52.9 | 231.8 |
| Controls | 0 | 52.5 | 59.0 | 163.2 |
| 12-n-propyl-10,11-dihydro-5,10-imino-[5H]-dibenzo (a,d) cycloheptene | 1 mg/Kg | 54.2 | 61.8 | 170.3 |
| | 2 mg/Kg | 50.4 | 57.3 | 225.8 |
| | 5 mg/Kg | 51.4 | 60.0 | 265.2 |
| | 10 mg/Kg | 57.7 | 78.4 | 275.9 |

TABLE II-continued

| Group | Dose Administred | Dose of pentamethylenetetrazol in mg/Kg | | |
|---|---|---|---|---|
| | | Myoclonia | Clonic Crisis | Tonic Crisis |
| dl | | | | |
| Controls | 0 | 42.2 | 49.2 | 127.7 |
| 8-chloro-12-methyl -10,11-dihydro-5, 10-imino-[5H]-dibenzo (a,d) cycloheptene dl fumarate | 5 mg/Kg 10 mg/Kg 20 mg/kg 50 mg/kg | 43.9 44.1 49.7 52.6 | 50.8 52.0 56.4 66.7 | 128 174.7 230.2 274.2 |
| Controls | 0 | 41.1 | 48.3 | 142.4 |
| 12-(2'-chloroethyl -10,11-dihydro-5, 10-imino-[5H]-dibenzo (a,d) cycloheptene dl | 2 mg/Kg 5 mg/Kg 10 mg/Kg | 45.9 51.5 57 | 52.9 56.7 62.1 | 163.2 229.8 258.2 |

Table II shows that the compounds tested possess an important anticonvulsant activity.

C. Potentialization of DOPA

In this test, DOPA [racemic β-(3,4-dihydroxyphenyl)-alanine] was administered to mice pretreated with 1-isonicotinoyl-2-isopropyl-hydrazine 18 hours before the test which product caused the following symptoms: hypertonicity, agitation, crying, aggressiveness, salivation and exophthalmia. The administration of an antidepressant one hour before the DOPA injection potentializes the intensity of the effects.

Male mice weighing between 18 to 22 g received intraperitoneally 50 mg/kg of 1-isonicotinoyl-2-isopropyl-hydrazine and 18 hours later the test product intraperitoneally in aqueous solution in increasing doses and 1 hour later received an intraperitoneal injection of 50 mg/kg of DOPA. The different effects were evaluated 15 and 30 minutes after the DOPA injection and each symptom was evaluated for each animal on a scale from 0 to 3 and the evaluations for each dose was totaled. The totals are reported in Table III as a percent of the total of control animals.

TABLE III

| Product of Example | Doses administred in mg/Kg | | | | | |
|---|---|---|---|---|---|---|
| | 1 | 2 | 5 | 10 | 20 | 50 |
| 21 | 187% | 175% | 181% | | | |
| 6 | 138% | 155% | 160% | 140% | | |
| 7 | 114% | 135% | 138% | 173% | | |
| 14 | | | | 117% | 160% | 196% |
| 29 | | | | 81% | 101% | 177% |
| 30 | | | | 113% | 150% | |

The results of Table III show that the compounds of the invention possess an important potentialization of DOPA activity.

D. Antidepressant Activity

The antidepressant activity was determined by antagonism exercised by the compounds against the depressant activity of reserpine and this effect was determined by ptosis of the eyelid test codified by Rubin [J. Pharm. Exp. Ther., Vol. 120 (1957), p. 125]. The eyelid ptosis test is used to make a quantitative evaluation of the condition of the animal, but the antagonism exercised equally against the neuro depressive symptoms of reserpine; immobility, adynamia, hypothermia, myosis, etc. The reading was effected every hour for 6 hours after intraperitoneal injection of 1 mg/kg of reserpine to groups of rats who had one hour previously received intraperitoneally a variable dose of the test compounds. The ptosis provoked by the reserpine injection was diminished by the previous injection of the test compounds, all the more so at the elevated doses. The results were expressed as a percentage of protection compared to controls which received only reserpine and are reported in Table IV.

TABLE IV

| Products | % Protection | | | |
|---|---|---|---|---|
| | 2 mg/Kg | 10 mg/Kg | 20 mg/Kg | 50 Mg/Kg |
| 12-(2'-methylaminoethyl)-10,11-dihydro-5,10-imido-[5H]-dibenzo (a,d) cycloheptene (compound I) | 10 | 43 | 60 | 84 |
| 12-(2'-dimethylaminoethyl)-10,11-dihydro-5,10-imino-[5H]-dibenzo (a,d) cycloheptene (fumarate) (compound II) | 9 | 40 | 39 | 66 |
| 12-(2' aminoethyl)-10,11-dihydro-5,10-imino-[5H - dibenzo (a,d) cycloheptene (compound III) | 18 | 38 | 69 | 74 |

The results of Table IV show that the dose that reduces by 50% ptosis of the eyelid provoked by reserpine ($DA_{50}$) is between 10 and 20 mg/kg for compounds I to III.

E. Potentialization of Sleeping Time

The potentialization of sleeping time was determined with a test using amytal [5-ethyl-5-isoamyl-barbituric acid] in which groups of female mice weighing between 18 and 22 g were kept at 25° C for the duration of the test. The test products were administered intraperitoneally at different doses one hour before intraveinous injection of 80 mg/kg of amytal and the sleeping time was noted which is the time while the reflux of straightening in the mice was negative. The average sleeping time for each group was determined in minutes and the results are reported in Table V.

TABLE V

| Doses administered | Controls | 0.5 mg/Kg | 1 mg/Kg | 2 mg/Kg | 5 mg/Kg | 10 mg/Kg | 20 mg/Kg | 50 mg/Kg |
|---|---|---|---|---|---|---|---|---|
| 12-propargyl-10,11-dihydro-5,10-imino-[5H]-dibenzo (a,d) cycloheptene | 35.0 | 41.8 | 46.5 | 49.4 | 64.9 | | | |
| 12-methyl-10,11-dihydro-5,10-imino-[5H]-dibenzo (a,d) cycloheptene | 27.9 | 33.9 | 32.9 | 30.6 | 42.9 | 78.6 | | |

TABLE V-continued

| Doses administered | Controls | 0.5 mg/Kg | 1 mg/Kg | 2 mg/Kg | 5 mg/Kg | 10 mg/Kg | 20 mg/Kg | 50 mg/Kg |
|---|---|---|---|---|---|---|---|---|
| 12-allyl-10,11-dihydro-5,10-imino-[5H]-dibenzo (a,d) cycloheptene | 40.8 | | | 37.1 | 65.1 | 71.7 | >120 | |
| 12-ethyl-10,11-dihydro-5,10imino-[5H]-dibenzo (a,d) cycloheptene | 30.3 | | 32.1 | 39.6 | 58.1 | 71.5 | | |
| 12-acetonyl-10,11-dihydro-5,10-imino-[5H]-dibenzo (a,d) cycloheptene | 21.7 | | | | 31.3 | 51.2 | 82.3 | 107.5 |
| 12-n-propyl-10,11-dihydro-5,10-imino-[5H]-dibenzo (a,d) cycloheptene | 32.4 | | | 38.6 | 42.2 | 65.1 | 103.7 | |
| 8-chloro-12-methyl-10,11-dihydro-5,10-imino-[5H]-dibenzo (a,d) cycloheptene (fumarate) | 12.1 | | | | 22.6 | 27.4 | 36.0 | 94.5 |
| 12-(2'-chloroethyl)-10,11-dihydro-5,10-imino-[5H]-dibenzo (a,d) cycloheptene | 23.9 | | | 21.7 | 42.2 | 44.8 | 83.0 | |
| 12-(2'-aminoethyl)-10,11-dihydro-5,10-imino-[5H]-dibenzo (a,d) cycloheptene | 31.5 | | | | 46.3 | 38.1 | 64.1 | 89.0 |

Table V shows that the test products potentialize the sleeping time provoked by amytal.

F. Acute Toxicity

The acute toxicity was determined on groups of Swiss mice weighing 18 to 22 g and the test products were administered intraperitoneally in increasing doses and the animals were kept under observation for a week. The $DL_{50}$ dose was then determined and is reported in Table VI.

TABLE VI

| Product of Example | $LD_{50}$ in mg/Kg |
|---|---|
| 8 | > 1000 |
| 7 | 350 |
| 10 | > 500 |
| 19 | 350 |
| 6 | 350 |
| 13 | 1000 |
| 9 | 350 |
| 17 | 1000 |
| 14 | 150 |
| 15 | ≃ 175 |
| 1 and 18 | 150 |
| 16 | > 200 |
| 24 | ≃250 |
| 25 | ≃300 |
| 26 | ≃350 |
| 27 | ≃150 |
| 28 | ≃150 |
| 29 | ≃180 |
| 30 | ≃150 |
| 23 | > 400 |

Various modifications of the composition and method of the invention may be made without departing from the spirit or scope thereof and it should be understood that the invention is to be limited only as defined in the appended claims.

We claim:

1. A compound selected from the group consisting of racemates and optically active isomers of a compound of the formula

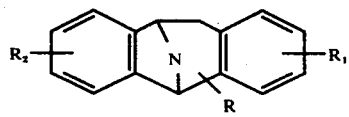

wherein R is selected from the group consisting of
—$(CH_2)_n$—$COCH_3$ where $n$ is O or 1,

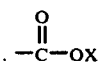

wherein X is selected from the group consisting of lower alkyl, phenyl, nitro-phenyl,
phenylalkyl of 7 to 8 carbon atoms,
acyl of a saturated aliphatic mono carboxylic acid of 1 to 6 carbon atoms optionally substituted with

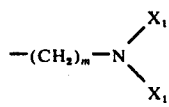

where $m$ is an integer from O to 6 and $X_1$ is selected from the group consisting of hydrogen and lower alkyl,

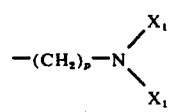

where *p* is an integer from 1 to 6 and $X_1$ is as before,

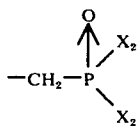

wherein $X_2$ is lower alkyl,
and $R_1$ and $R_2$ are individually selected from the group consisting of hydrogen, halogen, lower alkyl, lower alkoxy, $CF_3$- and diloweralkylamino and the non-toxic, pharmaceutically acceptable acid addition and quaternary ammonium salts thereof.

2. A compound of claim 1 wherein R is selected from the group consisting of hydrogen, methyl, ethyl, n-propyl and hydroxyethyl.

3. A compound of claim 1 selected from the group consisting of 12-(3'-dimethylaminopropyl)-10,11-dihydro-5,10-imino-[5H]-dibenzo (a,d)-cycloheptene and its non-toxic, pharmaceutically acceptable acid addition salts.

4. A compound of claim 1 selected from the group consisting of 12-dimethylaminoacetyl-10,11-dihydro-5,10-imino-[5H]-dibenzo (a,d)-cycloheptene and its non-toxic, pharmaceutically acceptable acid addition salts.

5. A compound of claim 1 selected from the group consisting of 12-methyl-10,11-dihydro-5,10-imino-[5H]-dibenzo (a,d)-cycloheptene and its non-toxic, pharmaceutically acceptable acid addition salts.

6. A compound of claim 1 selected from the group consisting of 12-(2'-methylaminoethyl)-10,11-dihydro-5,10-imino-[5H]-dibenzo (a,d)-cycloheptene and its non-toxic, pharmaceutically acceptable acid addition salts.

7. A compound of claim 1 selected from the group consisting of 12-(2'-dimethylaminoethyl)-10,11-dihydro-5,10-imino-[5H]-dibenzo (a,d)-cycloheptene and its non-toxic, pharmaceutically acceptable acid addition salts.

8. A compound of claim 1 selected from the group consisting of 12-(2'-aminoethyl)-10,11-dihydro-5,10-imino-[5H]-dibenzo (a,d)-cycloheptene and its non-toxic, pharmaceutically acceptable acid addition salts.

9. A composition for stimulating the central nervous system comprising an amount sufficient to stimulate the central nervous system of a compound selected from the group consisting of a compound of the formula

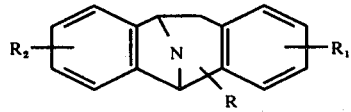

wherein R is selected from the group consisting of
hydrogen,
lower alkyl optionally substituted with hydroxy or halogen,
lower alkenyl,
lower alkynyl,
-(CH$_2$)$_n$COCH$_3$ where *n* is O or 1,

wherein X is selected from the group consisting of lower alkyl, phenyl, nitro-phenyl,
phenylalkyl of 7 to 8 carbon atoms,
acyl of a saturated aliphatic mono carboxylic acid of 1 to 6 carbon atoms optionally substituted with

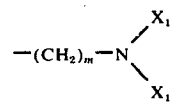

where *m* is an integer from O to 6 and $X_1$ is selected from the group consisting of hydrogen and lower alkyl,

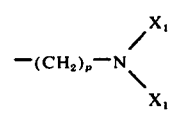

where *p* is an integer from 1 to 6 and $X_1$ is as before,

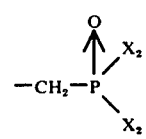

wherein $X_2$ is lower alkyl,
and $R_1$ and $R_2$ are individually selected from the group consisting of hydrogen, halogen, lower alkyl, lower alkoxy, $CF_3$- and diloweralkylamino and the non-toxic, pharmaceutically acceptable acid addition and quaternary ammonium salts thereof and an inert pharmaceutical carrier.

10. A method of stimulating the central nervous system of warm-blooded animals comprising administering to a warm-blooded animal a central nervous system stimulating amount of a compound selected from the group consisting of a compound of the formula

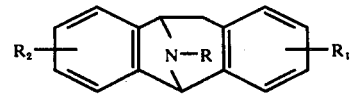

wherein R is selected from the group consisting of
hydrogen,
lower alkyl optionally substituted with hydroxy or halogen,
lower alkenyl,
lower alkynyl,
-(CH$_2$)$_n$—COCH$_3$ where *n* is O or 1,

wherein X is selected from the group consisting of lower alkyl, phenyl, nitro-phenyl,
phenylalkyl of 7 to 8 carbon atoms, acyl of a saturated aliphatic mono carboxylic acid of 1 to 6 carbon atoms optionally substituted with

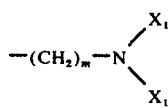

where *m* is an integer from 0 to 6 and $X_1$ is selected from the group consisting of hydrogen and lower alkyl,

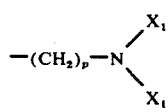

where *p* is an integer from 1 to 6 and $X_1$ is as before,

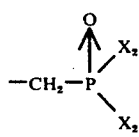

wherein $X_2$ is lower alkyl,
and $R_1$ and $R_2$ are individually selected from the group consisting of hydrogen, halogen, lower alkyl, lower alkoxy, $CF_3$- and diloweralkylamino and the non-toxic, pharmaceutically acceptable acid addition and quaternary ammonium salts thereof.

11. A method of treating the symptoms of Parkinson disease comprising administering to one suffering Parkinson disease an amount effective to relieve the said symptoms of a compound selected from the group consisting of a compound of the formula

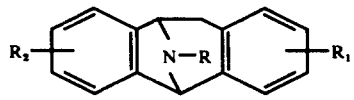

wherein R is selected from the group consisting of hydrogen,
lower alkyl optionally substituted with hydroxy or halogen,
lower alkenyl,
lower alkynyl,
-(CH$_2$)$_n$—COCH$_3$ where *n* is O or 1,

wherein X is selected from the group consisting of
lower alkyl, phenyl, nitro-phenyl,
phenylalkyl of 7 to 8 carbon atoms,
acyl of a saturated aliphatic mono carboxylic acid of 1 to 6 carbon atoms optionally substituted with

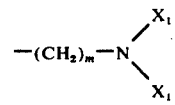

wherein *m* is an integer from 0 to 6 and $X_1$ is selected from the group consisting of hydrogen and lower alkyl,

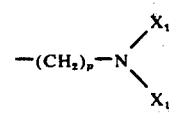

where *p* is an integer from 1 to 6 $X_1$ is as before,

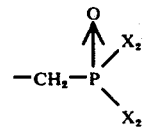

wherein $X_2$ is lower alkyl,
and $R_1$ and $R_2$ are individually selected from the group consisting of hydrogen, halogen, lower alkyl, lower alkoxy, $CF_3$- and diloweralkylamino and the non-toxic, pharmaceutically acceptable acid addition and quaternary ammonium salts thereof.

12. The method of claim 10 wherein R is selected from the group consisting of hydrogen, methyl, ethyl, n-propyl and hydroxyethyl.

* * * * *